United States Patent [19]

Vigne et al.

[11] Patent Number: 5,023,271

[45] Date of Patent: Jun. 11, 1991

[54] PHARMACEUTICAL MICROEMULSIONS

[75] Inventors: Jean-Louis Vigne, San Francisco; John P. Kane, Hillsborough, both of Calif.

[73] Assignee: California Biotechnology Inc., Mountain View, Calif.

[21] Appl. No.: 765,359

[22] Filed: Aug. 13, 1985

[51] Int. Cl.$^5$ ............... A61K 31/355; A61K 31/595; A61K 31/07; A61K 31/225

[52] U.S. Cl. ............................ 514/458; 514/168; 514/546; 514/547; 514/589; 514/681; 514/725; 514/788

[58] Field of Search ............... 514/168, 458, 681, 725, 514/788

[56] References Cited

U.S. PATENT DOCUMENTS

| | | | |
|---|---|---|---|
| 3,384,545 | 5/1968 | Alello et al. | 167/81 |
| 4,158,707 | 6/1979 | Steffen et al. | 424/244 |
| 4,271,196 | 6/1981 | Schmidt | 424/358 |
| 4,328,222 | 5/1982 | Schmidt | 424/244 |
| 4,377,567 | 3/1983 | Geho | 252/316 |

FOREIGN PATENT DOCUMENTS

57-163313  10/1982  Japan .

OTHER PUBLICATIONS

Chem. Abst. 100:145017(d) (1984)-Eisai Co. Ltd.
Chem. Abst., 98:95647(b) (1983)-Daigo Muti. Chem.
Chem. Abst. 95:138633(b) (1981)-Teikoku Chem. Ind.
Bauernfeind, J. C., et al., *Am. J. Clin. Nutr.* (1974), 27:234-253.
Bodenstein, C. J., *Pediatrics* (1984), 73:733.
Caravaggi, C., et al., *N.Z.J. Agric. Res.* (1968), 11:313-318.
Erin, A. N., et al., *Biochim. et Biophys. Acta* (1984), 774:96-102.
Gutcher, G. R., et al., *J. Parent. & Enteral. Nutr.* (1984), 8:269-273.
Whitin, J. C., et al., *J. Lipid Res.* (1982), 23:276-282.
Bieri, J. G., et al., *Am. J. Clin. Nutr.* (1977), 30:686-690.
Bjornson, L. K., et al., *J. Lipid Res. (1976),* 17:343-352.
Davies, T., et al., *Clin. Chim. Acta* (1969), 24:431-436.
Kritchevsky, D., et al., *Nutr. Repts. Intl.* (1980), 225:339-342.
Kayden, H. J., *Tocopherol, Oxygen and Biomembranes,* C. de Duve and O. Hayashi, eds. (1978), pp. 131-142.
Murphy, D. J., et al., *J. Biol. Chem.* (1981), 25:10464-10468.
Stamper, M. J., et al., *Am. J. Clin. Path.* (1983), 79:714-716.
Underwood, B. A., et al., *Ped. Res.* (1972), 6:26-31.
Gallo-Torres, H. E., et al., *Intl. J. Vit. Nutr. Res.* (1971), 41:339-354.
Chen, G. C., *Biochem.* (1984), 23:6530-6538.

*Primary Examiner*—Jerome D. Goldberg
*Assistant Examiner*—Raymond J. Henley, III
*Attorney, Agent, or Firm*—Irell & Manella

[57] ABSTRACT

A method for parenteral administration of fat-soluble pharmaceuticals and vitamins using microemulsions is disclosed. The microemulsions are comprised of a naturally occurring amphipatic substance and a hydrophobic lipid along with the active ingredient, are size selected for 300-1000 Å pseudomicelles, and permit safe intravenous injection of the active ingredient. Levels of the active ingredient in the various lipoprotein fractions of serum appear to mimic the natural distribution of the administered drug if taken orally.

11 Claims, 3 Drawing Sheets

PHARMACEUTICAL MICROEMULSIONS

TECHNICAL FIELD

The invention relates to the administration of compositions containing effective amounts of fat soluble vitamins or drugs. In particular, the invention relates to microemulsions suitable for parenteral administration of vitamins E, A, D, and K and hydrophobic pharmaceuticals.

BACKGROUND ART

The administration of fat soluble vitamins and pharmaceuticals becomes a medical problem when deficiencies in or needs for these substances are displayed by subjects not capable of normal intestinal absorption of these vitamins into the bloodstream. While normal children and adults can employ commercially available oral compositions, such as old-fashioned cod liver oil, to obtain needed supplements of fat soluble vitamins, individuals with malabsorption and premature infants require parenteral administration in order to make dosage effective. Similarly, while the majority of people can take oral formulations of fat-soluble drugs, often those most in need of them—i.e., seriously ill patients, are often not capable of swallowing or otherwise employing the normal gastrointestinal process.

In particular, for example, attention has been focused on the administration of α-tocopherol (vitamin E), because administration by non-oral routes has led to serious problems. It is rare for simple nutritional deprivation of this vitamin to cause a deficiency in humans. Adults with normal metabolism apparently store sufficient vitamin E to weather long periods of diminished intake. The function of the vitamin is largely unknown, but it appears to be localized in the membranes in association with highly unsaturated fatty acids and there is, at present, a concensus that the vitamin stabilizes these membranes, at least in part by virtue of its anti-oxidant properties and by virtue of its formation of complexes with free fatty acids (Erin, A. N., et al, *Biochim et Biophys Acta* (1984) 774:96-102; Whitin, J. C., et al, *J Lipid Res* (1982) 23:276-282). The most readily demonstrated effect of vitamin E deficiency is an in vitro erythrocyte hemolysis in the presence of hydrogen peroxide; the clinical symptoms are associated with loss of integrity of the membranes of the various physiological systems both in humans and in animals.

Vitamin E deficiency in humans is most often encountered in premature infants and in adults or children with abnormal rates of absorption of fats from the intestine, thus necessitating parenteral administration. The importance of vitamin E administration in premature infants has increased measurably over the past several decades as the number of such infants maintained viable has greatly increased. Administration of vitamin E is particularly important to counterbalance the negative effects of the administration of oxygen. Oxygen is directly beneficial in treating infants with hyaline membrane disease, but has a side effect of severe damage to the retina. It is believed by some investigators that adequate levels of vitamin E can mitigate this. However, oral administration of vitamin E to these infants results in gastrointestinal problems and intravenous administration has been implicated in several neonatal deaths (Bodenstein, C. J., *Pediatrics* (1984) 73:733). Current products for such parenteral administration are aqueous emulsions which contain detergents as the emulsifying agent.

In addition, with respect to vitamin E per se, a small group of individuals with a genetic hereditary disorder, abetalipoproteinemia, i.e., who lack plasma β-lipoprotein, also exhibit the need for parenteral vitamin E. Finally, severe malnutrition, especially in infants and children, results in a deficiency which warrants parenteral administration of this vitamin, and patients subjected to trauma requiring administration of high levels of oxygen may benefit from its anti-oxidant properties.

Individuals with malabsorption syndromes in general exhibit a need for parenteral administration of fat soluble vitamins and drugs. These individuals include patients suffering from cystic fibrosis, chronic pancreatitis, pancreatic carcinoma, cirrhosis of the liver, glutin enteropathy, tropical sprue, regional enteritis, ulcerative colitis, and persons who have been subjected to gastrointestinal surgery. All of these individuals are inadequately capable or incapable of proper transport of orally administered fat soluble nutrients and pharmaceuticals to the bloodstream for subsequent metabolic utilization.

While the foregoing discussion has focused on deficiencies of vitamins or the need for therapy using fat soluble substances in humans, it is recognized that other mammals may also benefit from suitable parenteral administration of dietary supplements containing fat soluble vitamins and may require similar therapy.

Presently known routes of administration are less than perfect. There have been reports of intramuscular administration of vitamin E in the veterinary field (Caravaggi, C., et al, *N.Z.J. Agric Res* (1968) 11:313–318), however the effectiveness of this route in transporting the vitamin to the bloodstream appears to vary with the nature of the subject. Intramuscular administration has also been used in humans (Bauernfeind, J. C., et al, *Am J Clin Nutr* (1974) 27:234–253). However, most emphasis for parenteral dosing has been placed on intravenous administration. Two commercially available preparations, Intralipid (soybean oil based), disclosed in U.S. Pat. No. 3,169,094, and Liposyn (safflower oil based) have been used, but they have been shown to be relatively poor sources of vitamin E (Gutcher, G. R., et al, *J Parent & Entreal Nutr* (1984) 8:269–273). U.S. Pat. No. 3,384,545 discloses an aqueous emulsion utilizing the polyoxyethylene ether of castor oil as an emulsifying agent. Other compositions have used detergents such as polysorbates. None of these compositions is satisfactory and their performance record in trouble-free administration of active ingredients has been poor.

The composition of the present invention has the unique property of delivering fat soluble substances to the plasma in a form and distribution which mimics that naturally occurring in normal subjects. It is therefore free of the problems encountered in the compositions presently known in the art. In addition, in certain embodiments, the carrier in the composition serves as a source of essential nutrients.

DISCLOSURE OF THE INVENTION

The compositions of the invention provide safe and effective delivery of fat soluble substances, for example, of vitamin E, to the circulatory system in a form which is readily recognized by the host. Accordingly, the vitamin or other substance is treated as in the normal course of metabolism, and no destructive side effects are found. This is accomplished by supplying the desired fat soluble substance in a microemulsion wherein the pseudomicelles are of such size and density as to mimic the chylomicron particles normally formed by fats transported across the intestinal wall. The small chylomicron pseudomicelles are on the order of 1,000 Å in diameter and are essentially fat globules surrounded by a hydrophilic surface which is generated from a monolayer of amphipatic molecules. The particles are sufficiently small to enter the liver, which appears to play a significant role in the distribution and utilization of a number of vitamins and drug metabolites. They are sufficiently large to prevent the side effect of hypercholesterolemia, a reaction often associated with use of liposomes (50-100 Å) to administer drugs. Microemulsions have in fact been used to model the lipoprotein components of plasma (Chen, G. C., et al, *Biochemistry* (1984) 23:6530-6538).

Thus, in one aspect, the invention relates to a composition comprising an effective amount of a fat soluble active ingredient harbored in a microemulsion of pseudomicelles 300-1,000 Å in diameter. Microemulsions containing pseudomicelles of this diameter generally have densities of approximately 1.005-1.1 g/ml, but the density range depends on the nature of the composition components. The final percentage composition of the microemulsion depends on particle size and the nature of the components. To prepare the microemulsion, initial ranges of about 40%-70% by weight of hydrophobic lipid, and 30%-60% by weight of a naturally occurring amphipatic substance are practical.

In other aspects, the invention relates to methods of administering fat soluble substances using the composition of the invention and to methods of preparing this composition.

MODES OF CARRYING OUT THE INVENTION

A. Definitions

Figure 1A:
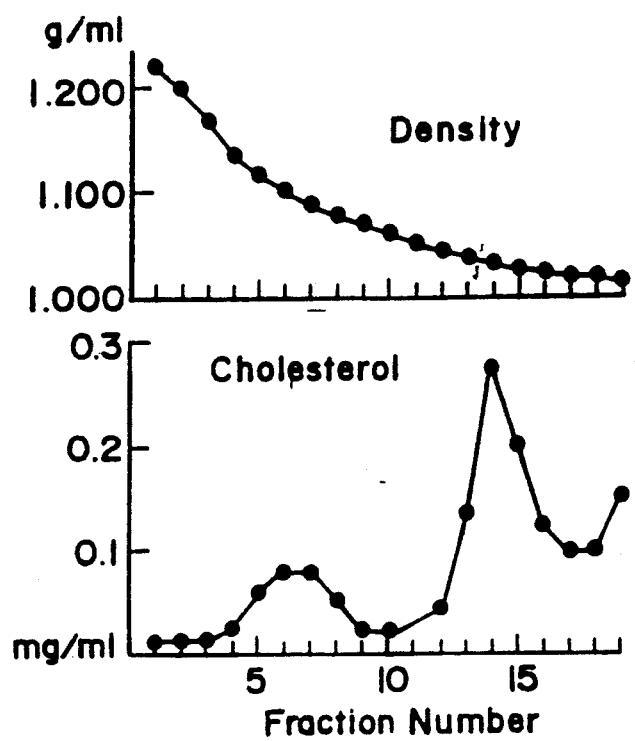
FIG. 1 shows the results of an in vitro assay whereby tocopherol contained in microemulsions of the invention distributes itself among the lipoprotein components of serum.

As used herein "microemulsion" refers to an aqueous suspension of pseudomicelles which contain relatively hydrophobic lipid centers surrounded by a monolayer of amphipatic (sometimes spelled amphipathic) molecules bearing hydrophilic moieties. In the microemulsions of the invention, the diameter of the pseudomicelles is approximately 300-1,000 Å. The nature of the particle is different from that of liposomes, which are unilamellar or multilamellar particles of bilayers, wherein the bilayers have hydrophilic surfaces on either side. Thus, liposomes have hydrophilic interiors as well as exteriors and are generally of smaller dimension—i.e., of the order of 50-100 Å.

"Pseudomicelles" by definition, differ from "micelles". Micelles are aggregations of amphipatic molecules—i.e., molecules which have both hydrophobic and hydrophilic portions such that the outer layer of the micelles is compatible with the surrounding medium. In a typical case, micelles in aqueous medium contain hydrophilic surfaces and hydrophobic interiors. Pseudomicelles have these characteristics, but differ in that the hydrophobic interiors are supplemented with additional hydrophobic material.

Micelles are generally very small in diameter (about 50-100 Å, similar to liposomes). Pseudomicelles can be substantially larger, depending upon the quantity of hydrophobic "filler" used in their centers. As the particles become larger, they become, in general, less dense as the low density hydrophobic fillers become a greater and greater proportion of the composition. Since the quantity of the hydrophobic center increases as the cube of the radius while that of the more dense hydrophilic surface layer increases only as the square, the ratio of the less dense hydrophobic material to the more dense amphipatic molecules making up the surface becomes larger.

In summary, pseudomicelles are comprised of amphipatic molecules on their surfaces, oriented so that the hydrophilic portions of the amphipatic surface molecules face the medium, and a hydrophobic core. In terms of definition, as used herein, "amphipatic" substances are those which have hydrophobic and hydrophilic portions. The amphipatic substances used in the compositions of the present invention are those which are found in the biosystem. Naturally occurring substances are used because, as explained below, many synthetic amphipatic materials—i.e., detergents, are toxic. The most commonly occurring amphipatic substances are the phospholipids, among which the lecithins are preferred.

"Lecithin" refers to a phospholipid derived from glycerol. Two of the glycerol hydroxyls are esterified to two long chain (8-24C) fatty acids. The third hydroxyl is one of the two alcohols of a phosphodiester; a tertiary amino alcohol is the other alcohol component. Thus, lecithins generally have the formula

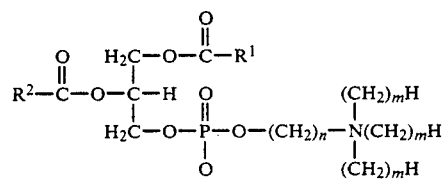

wherein $R^1$ and $R^2$ are independently hydrocarbyls of 7-23 carbons; n is an integer from 2-4 and each m is independently an integer of 1-4. Naturally occurring lecithins generally are comprised of choline esterified to the phosphate—i.e., n is 2 and all m are 1. In addition, in naturally occurring lecithins, $R^2$ is unsaturated and the glycerol carbon to which it is attached has the R configuration, as shown. In the lecithins employed in the invention, racemic mixtures as well as resolved enantiomers may of course be employed. Chirality of the center carbon of the glycerol is not relevant to the properties exhibited by the lecithins used in the invention.

Common biological sources for lecithins include soybean and egg yolk. Also functional, though less effective, are the ethanolamine analogs of the lecithins (cephalins) and more complex bipolar lipids such as sphingomyelins.

Of importance in determining the effectiveness of the amphipatic molecule is the degree of polarity provided by the hydrophilic portion. It is recognized that polarity is, in general, a sliding scale where no sharp boundaries are found. However, there is a clear difference in class when a readily ionizable hydrogen is present. Thus, phospholipids, which contain an ionized phosphate diester at neutral pH, contain clearly polar portions along with the long chain fatty acid hydrophobic portions. However, even the monoglycerides (which contain two free hydroxyl groups) are amphipatic, although to a lesser extent. Strictly speaking, even the triglycerides which are included in the definition below as "hydrophobic" lipids contain a moderately polar region in the glycerol region. However, the polarity of the triester is not sufficient to render the whole amphipatic.

"Hydrophobic lipid" refers to a lipid which is not sufficiently amphipatic to stabilize an emulsion. Triglycerides are classic examples. When mixed with water, the momentary suspension of lipid particules in the aqueous medium immediately separates into two homogeneous oil and water layers. Of particular relevance to the invention is the observation that triglycerides, vitamin A acetate and tocopherol acetate (the acetylated form of vitamin E) behave as hydrophobic lipids, and can form the pseudomicelle core.

As set forth above, the pseudomicelles of the invention are thus envisioned as containing amphipatic outer layers wherein the amphipatic substances are oriented with their hydrophilic portions facing outward, and are filled with hydrophobic substances in the core. The active ingredient included in the pseudomicelles will distribute itself within the pseudomicelle according its own polarity characteristics. Fat soluble substances which are substantially entirely hydrophobic are found mostly in the core. Moderately polar fats such as vitamin E itself, vitamin K and vitamin A, and steroid compounds containing hydroxyl groups such as vitamin D and cholesterol distribute themselves more densely in the boundary between the surface molecules and the core or in the surface monolayer. Any classification of the active ingredient into "hydrophobic" lipid or "amphipatic" is to a large extent arbitrary. There will be a continum of distributions between the boundary layer and the core. In some cases, the active ingredient can serve as the boundary layer or the core.

B. General Method

The compositions of the invention are capable of effecting the distribution of a fat soluble active ingredient in plasma in a manner which mimics that encountered in the normal physiology of the subject. With respect to vitamin E specifically, there has been considerable study of the normal transport of this vitamin in plasma.

A summary of the distribution of $\alpha$-tocopherol in the serum lipoproteins and various cellular components in blood was published by Kayden, H. J., *Tocopherol, Oxygen, and Biomembranes* (1978) Elsevier/North Holland Biomedical Press, pp 131–142. The total tocopherol in plasma, as opposed to that of the cellular components, seems correlated to the total lipid content of the plasma. However, the variation found in erythrocytes, platelets, lymphocytes, and granulocytes parallels the variation of tocopherol in plasma as altered by increased oral intake of this vitamin. Tocopherol was found to be associated with all the lipoprotein components of plasma, but had a higher correlation with the low density lipoproteins (LDL) in humans than with the other two major lipoprotein constituents, high density lipoproteins (HDL) and very low density lipoproteins (VLDL). In other species the distribution may be different. (The lipoprotein components of the blood are classified according to their densities (Havel, R. J., et al, *J Clin Invest* (1955) 34:1345–1353). While there are no sharp boundaries, there appear to be clusters of lipoprotein components in the gradient. The VLDL has a density range of approximately 0.95–1.006 g/ml; LDL of approximately 1.006–1.063 g/ml; and HDL of approximately 1.063–1.21 g/ml.)

As tocopherol appears to be functional in the context of membranes, studies have also been made concerning the transfer of this vitamin into the membrane structure. For example, Murphy, D. J., *J Biol Chem* (1981) 256:10464–10468 showed that components of the rat liver cytosol mediate the transfer of tocopherol between membranes including transfer from an in vitro liposome preparation to liver microsomes. It would appear that each fat soluble vitamin or drug has its own transport system in the plasma as exemplified, for example, by the differences shown for $\alpha$-tocopherol and $\beta$-carotene in human blood by Bjornson, L. K., et al, *J Lipid Res* (1976) 17:343–352. A further paper shows the transfer of d-$\alpha$-tocopherol from the plasma to a receptor protein in rat liver nuclei (Nair, P. P., et al *Tocopherol, Oxygen & Biomembranes*, (1978, supra) pp 121–130).

Plasma transport of the active ingredient of an orally administered composition is a precursor to the manifestation of biological activity at the intended sites. This transport is normally initiated by transfer of chylomicron particles comprising the active ingredient in question across the intestinal walls. However, there are a number of instances, as outlined above in the case of vitamin E, and applicable as well to other fat soluble pharmaceuticals, wherein oral administration is undesirable and the vitamins or drugs must be administered parenterally, preferably intravenously. In these cases, the natural assembly of the chylomicron particles is bypassed and whatever form is injected must substitute for them as a vehicle.

In general, in order to inject liquid compositions containing fat soluble materials, measures must be taken to assure a uniform suspension of the desired substance in water. A number of approaches have been taken toward this result. One recently popular general technique involves the formation of liposomes to behave as carriers of the active ingredient. Two characteristics make such particles unsuitable in this case. First, since the multi- or unilamellar liposomes are composed of bilayers with hydrophilic boundaries, they are more hospitable to polar substances than to lipophilic materials. Second, the liposome particles tend to be quite small. Since they are only of the order of 50–100 Å, they have a high concentration of amphipatic substance at their surfaces. These substances are capable of solubilizing cholesterol from the cell membranes and inducing hepatic cholesterol synthesis. Liposomes can thus cause hypercholesterolemia (Byers, S. O., et al, *J Biol Chem* (1962) 237:3375–3380; Jakoi, L., et al, *J Biol Chem* (1974) 269:5840–5844).

Another approach has been to use synthetic detergents to solubilize lipid soluble substances. Detergents mediate the interaction between lipophiles and aqueous medium at a molecular level and are thus able to provide a uniform distribution. However, many detergents are toxic when used in effective amounts. For example, materials such as sodium lauryl sulfate (SDS) and Triton X-100 are not usable in solutions to be administered to mammalian subjects. Less toxic detergents such as polysorbate 80 and its derivatives are more appropriate, but nevertheless appear to constitute a health hazard.

In the approach of the present invention, a microemulsion is used as a carrier for the active ingredient. To obtain the microemulsion, a naturally occurring amphipatic substance is used as an emulsifying agent to form the boundary layer of pseudomicelles in the presence of sufficient hydrophobic lipid to form the cores. Selection is made to obtain pseudomicelles approximately 300–1,000 Å in diameter. This size particle is sufficiently small to undergo uptake by the liver, as is the normal course of fatty substance metabolism, but is large enough to be capable of containing effective amounts of active ingredients and to minimize the hypercholesterolemia which occurs at high concentrations of amphipatic substances.

The pseudomicelles are formed by mixing active ingredient, hydrophobic lipid material, and naturally occurring amphipatic substance in a ratio suitable to generate a large proportion of pseudomicelles of the proper size. (An approximate exemplary ratio is 5:40:55 by weight for vitamin E, tocopherol acetate, and lecithin, for example.) The workable starting ratio has no precise limits and can vary widely, but yields are increased if the initial ratio approximates that in the final pseudomicelle composition. The suspension is then sonicated to form a mixture of various size pseudomicelles. The sonicated suspension is then subjected to gradient density segregation and those pseudomicelles having the approximate density of 1.005–1.1 g/ml depending on the nature of the components are selected from the gradient to obtain particles of 300–1,000 Å diameter. These pseudomicelles contain the very approximate original composition of the mixture, if the above exemplified ratio is used for the illustrated components, and are used directly for administration of the active ingredient.

Exemplary embodiments of the hydrophobic lipid which is used to form the core portion include vitamin A acetate, tocopherol acetate, triglyceride preparations, or combinations thereof. Preferred embodiments of the naturally occurring amphipatic substance include lecithin, e.g., phosphatidylcholine which can be obtained from egg yolk, other phospholipids and partial glycerides. Active ingredients (which distribute according to their own character between the boundary and core) include tocopherol, tocopherol acetate, vitamin A, vitamin E, vitamin D, phenesterine, daunorubicin, doxorubicin, mitotane, visadine, halonitrosoureas, anthrocyclines, hydrophobic proteins, ellipticine or combinations thereof, and diazepam. Of course, mixtures of these active ingredients can be used. The active ingredient will distribute in the pseudomicelle according to its character on the amphipatic/hydrophobic scale. Some active ingredients, such as tocopherol acetate are sufficiently hydrophobic to be used as the hydrophobic lipid in forming the core. Others, such as vitamin A, are sufficiently amphipatic to form the boundary. In these instances, the active ingredient may be used simultaneously as a part of the carrier, as well as for its activity. In addition, if triglycerides are used as the hydrophobic lipid, they are hydrolyzed and metabolized as nutrients. Similarly, if vitamin A acetate or tocopherol acetate are used as core, they are hydrolyzed to the active vitamins.

C. Administration and Use

For administration, the compositions of the invention are injected into a human or animal subject intravenously in an amount suitable for the condition being treated and the subject. As a general proposition, the amount of active ingredient will often be on the order of approximately 1%–10% of the total content of microemulsion in the suspension depending on the amount desired to be administered. However, if the active ingredient is a "hydrophobic lipid" or sufficiently amphipatic to form the boundary, the percentage can be increased—i.e., the active ingredient can itself form the lipid core or the boundary layer.

When injected intravenously, the active ingredient contained in the microemulsion is transferred to the blood lipoproteins in a manner entirely analogous to that observed for orally administered dosages of the same material. Therefore, the pseudomicelles of the invention are capable of effectively placing the active substance into its normal progress of physiological activity.

D. Examples

The following examples are intended to illustrate but not to limit the invention.

The compositions of Examples 1–10 were prepared using the following general procedure: The active ingredient, if necessary dissolved in alcohol, is mixed with a suitable hydrophobic lipid such as soybean oil, triglyceride, or tocopherol acetate along with the amphipatic substance. The by weight percentages in the starting material for the active ingredients are about 1%–10% of the active ingredient (if it is used as active ingredient per se) up to about 60%–70% if the active ingredient can also serve as part of the boundary layer or core. The starting composition overall includes about 40%–70% of a hydrophobic lipid and about 30%–60% of an amphipatic substance. Thus, if the active ingredient is itself, for example, a hydrophobic lipid, this core-forming component of the mixture can be included as the active ingredient and thus enhance the dosage level by nearly a factor of 10, if this is desired.

The ingredients were pipetted into a pyrogen-free glass tube and the solvent was evaporated using a rotary evaporator. The dried lipids are resuspended in 5 ml of saline pH 7.4, buffered with 20 mM sodium phosphate, and the cloudy suspension is sonicated for 1 hr at 55° C. under a stream of nitrogen. (Sonication may be performed with a W-225 R sonicator (Ultrasonics Inc.) for example.)

The sonicated emulsion is purified by ultracentrifugal flotation in a three-layered discontinuous sucrose gradient in the tube of a Beckman SW41 rotor. The tube is centrifuged at 28,000 rpm at 10° C. for 60 min and the gradient is collected into 12 fractions labeled 1–12 from bottom to top of the tube. In all cases, fractions of approximately 6–10 as noted specifically in the examples were collected and contained microemulsions having a density which averaged 1.010–1.1 g/ml. In all cases the purified fractions were free from liposomes.

EXAMPLE 1

The original mixture contained:
5 mg α-tocopherol (dl) in ethanol;
40 mg α-tocopherol (dl) acetate in ethanol; and
55 mg of egg phosphatidylcholine type III in ethanol.

The gradient fractions recovered were 7–10 and had an average density of 1.02 g/ml and an average particle size of 700 Å.

The composition of the pseudomicellular compartments was 6.5% tocopherol; 45.5% tocopherol acetate; and 48% lecithin. In this and subsequent examples the tocopherol and tocopherol acetate quantitations were determined by reverse phase HPLC (Perkin-Elmer $C_{18}$) using a mobile phase of methanol:water on 97:3 v/v and phospholipids were determined by the method of Takayama, et al, *Clin Chim Acta* (1977) 79:93–98.

EXAMPLE 2

The original mixture contained:
5 mg α-tocopherol in ethanol;
40 mg soybean oil; and
55 mg phosphatidylcholine (egg yolk type III) in ethanol.

Fractions 8–11 were collected and microemulsion had an average density of 1.010 g/ml and an average diameter of 840 Å.

The resulting particles had the composition of 5.3% α-tocopherol; 17.4% lecithin; and 77.3% triglyceride.

EXAMPLE 3

The original mixture contained:
10 mg α-tocopherol (dl) in ethanol;
35 mg α-tocopherol (dl) acetate in ethanol; and
55 mg of egg phosphatidylcholine type III in ethanol.

The gradient fractions recovered were 7–10 and had an average density of 1.020 g/ml and an average particle size of 710 Å.

EXAMPLE 4

The original mixture contained:
45 mg tocopherol acetate in ethanol; and
55 mg of egg phosphatidylcholine type III in ethanol.

The gradient fractions recovered were 7–10 and had an average density of 1.025 g/ml and an average particle size of 700 Å.

EXAMPLE 5

The original mixture contained:
2 mg α-tocopherol in ethanol;
40 mg vitamin A acetate in ethanol; and
58 mg of egg phosphatidylcholine type III in ethanol.

The gradient fractions recovered were 7–10 and had an average density of 1.020 g/ml and an average particle size of 750 Å.

EXAMPLE 6

The original mixture contains:
10 mg α-tocopherol in ethanol;
25 mg vitamin A acetate in ethanol; and
65 mg of egg phosphatidylcholine type III in ethanol.

The gradient fractions recovered are 7–10 and had an average density of 1.025 g/ml and an average particle size of 700 Å.

EXAMPLE 7

The original mixture contains:
2.5 mg α-tocopherol in ethanol;
2.5 mg vitamin A in ethanol;
65 mg soybean oil; and
30 mg of egg phosphatidylcholine type III in ethanol.

The gradient fractions recovered are 8–11 and had an average density of 1.01 g/ml and an average particle size of 800 Å.

EXAMPLE 8

The original mixture contains:
5 mg α-tocopherol in ethanol;
2 mg vitamin $D_2$ in ethanol;
2 mg vitamin $K_1$ complex in ethanol;
61 mg vitamin A acetate in ethanol; and
30 mg of egg phosphatidylcholine type III in ethanol.

The gradient fractions recovered are 6–10 and had an average density of 1.015 g/ml and an average particle size of 750 Å.

EXAMPLE 9

The original mixture contains:
10 mg of BCNU (a nitrosourea, in particular Carmustine ™, Merck Index) in 50% ethanol;
40 mg egg phosphatidylcholine type III in ethanol; and
50 mg soybean oil;

The gradient fractions recovered are 8–11 and had an average density of 1.010 g/ml and an average particle size of 900 Å.

EXAMPLE 10

Vitamin E Transfer from Microemulsion to Plasma

The microemulsion prepared in Example 1 was treated with human and rabbit serum and the resulting mixtures were underlayered in a sodium chloride gradient. The diffusion of tocopherol in the mixtures was compared with the distribution of lipoproteins in the same mixtures and with the distribution of tocopherol from the untreated emulsion.

Figure 1B:
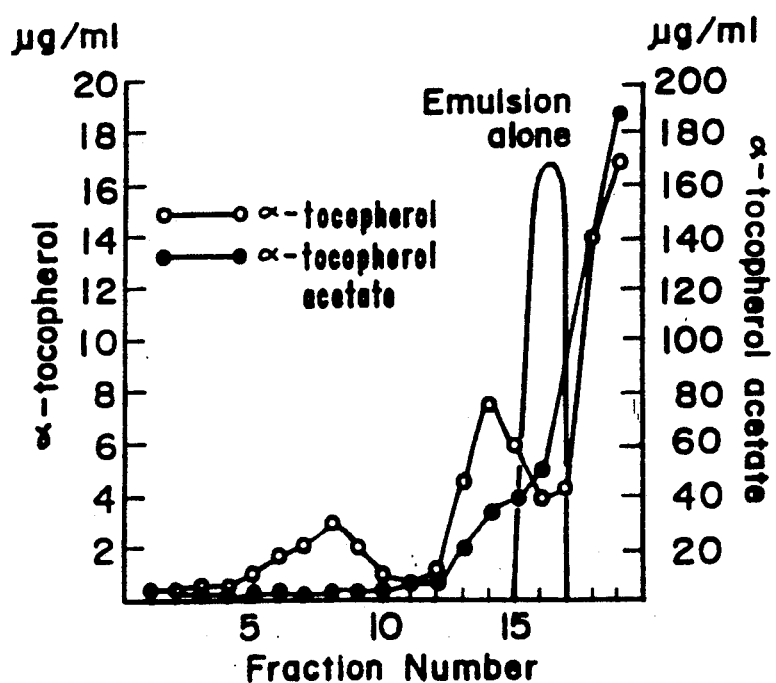

In more detail, 900 µl of human serum was incubated with 100 µl of the microemulsion of Example 1 for 1 hr at 37° in a shaker bath. For a control, 100 µl of the microemulsion were incubated with 900 µl of saline solution under the same conditions. Each mixture was underlayered in a sodium chloride gradient and separated by ultracentrifugation according to Foreman, et al, *J Lipid Research* (1977) 18:759–767. The fractions of various densities were collected and each fraction was assayed for the content of tocopherol, tocopherol acetate, and cholesterol. The results are shown in FIG. 1. The microemulsion alone mixed with saline gives a single peak for tocopherol at a density of approximately 1.018 g/ml. The tocopherol from the microemulsion mixed with serum, however, distributes itself in a pattern which is similar to that of cholesterol, thus indicating its distribution among the HDL, LDL, and VLDL fractions. The treatment of microemulsion with serum effects the transfer of the tocopherol to serum in conjunction with the lipoprotein content thereof. Similar results are obtained with rabbit serum.

EXAMPLE 11

Stability of Tocopherol Acetate

Nine hundred µl of normal human serum and 100 µl of the microemulsion of Example 1 were incubated at 37° C. in a shaker bath and samples were withdrawn every 30 min up to 2 hr. During this period of time, the ratio of α-tocopherol to tocopherol acetate was unchanged indicating that hydrolysis of the acetate to the free vitamin was extremely slow. The results were the same when heparin treated human serum was used. This is in contrast to the results in vivo as set forth below.

EXAMPLE 12

Transfer of Vitamin E from the Microemulsion to Plasma in Vivo

A. Short Term Results

Fifteen ml of the preparation of Example 1 were injected intravenously to New Zealand male rabbits and the levels of α-tocopherol and tocopherol acetate in the bloodstream were determined periodically over a period of 4 hr. The rabbits were then sacrificed and the tissues analyzed for their content of tocopherol and tocopherol acetate.

The results of the serum analysis showed that after 5 min, the levels of tocopherol in the blood had risen to approximately 40 µg/ml or approximately 10 times normal. The concentration then slowly decreased linearly to about 20 µg/ml over a period of 4 hr. The α-tocopherol acetate after 5 min was at a level of 280 µg/ml or about 70 times the normal α-tocopherol level, and then decreased slowly, finally disappearing from the circulation by the end of the 4 hr period.

The serum samples were also layered under a sodium chloride gradient and centrifuged. The distribution of the injected α-tocopherol and tocopherol acetate among the lipoprotein fractions was assessed. While the tocopherol acetate remained mainly at the density of the microemulsion alone, vitamin E was transferred, apparently to the LDL fraction, in exchange for cholesterol.

Analysis of the tissues showed accumulation of α-tocopherol in the liver, and to a lesser extent in the spleen. After 4 hr no α-tocopherol acetate could be detected in liver, spleen, and other tissues.

B. Long Term Results

New Zealand male rabbits were injected daily with 1 ml doses of the preparation of Example 1 for 30 days. Serum samples taken at 1 week intervals showed elevated levels of α-tocopherol and no change in cholesterol concentration. No tocopherol acetate was detectable in any of the samples.

In other experiments, rats were injected IV with 1 ml of the preparation of Example 1. The animals were sacrificed at 15 minute intervals for the first hour, after two hours, and then after 1, 3, 5, and 10 days. The levels of α-tocopherol and tocopherol acetate were assayed in the sera and liver extracts. The results are shown in FIGS. 2 and 3.

Figure 2:
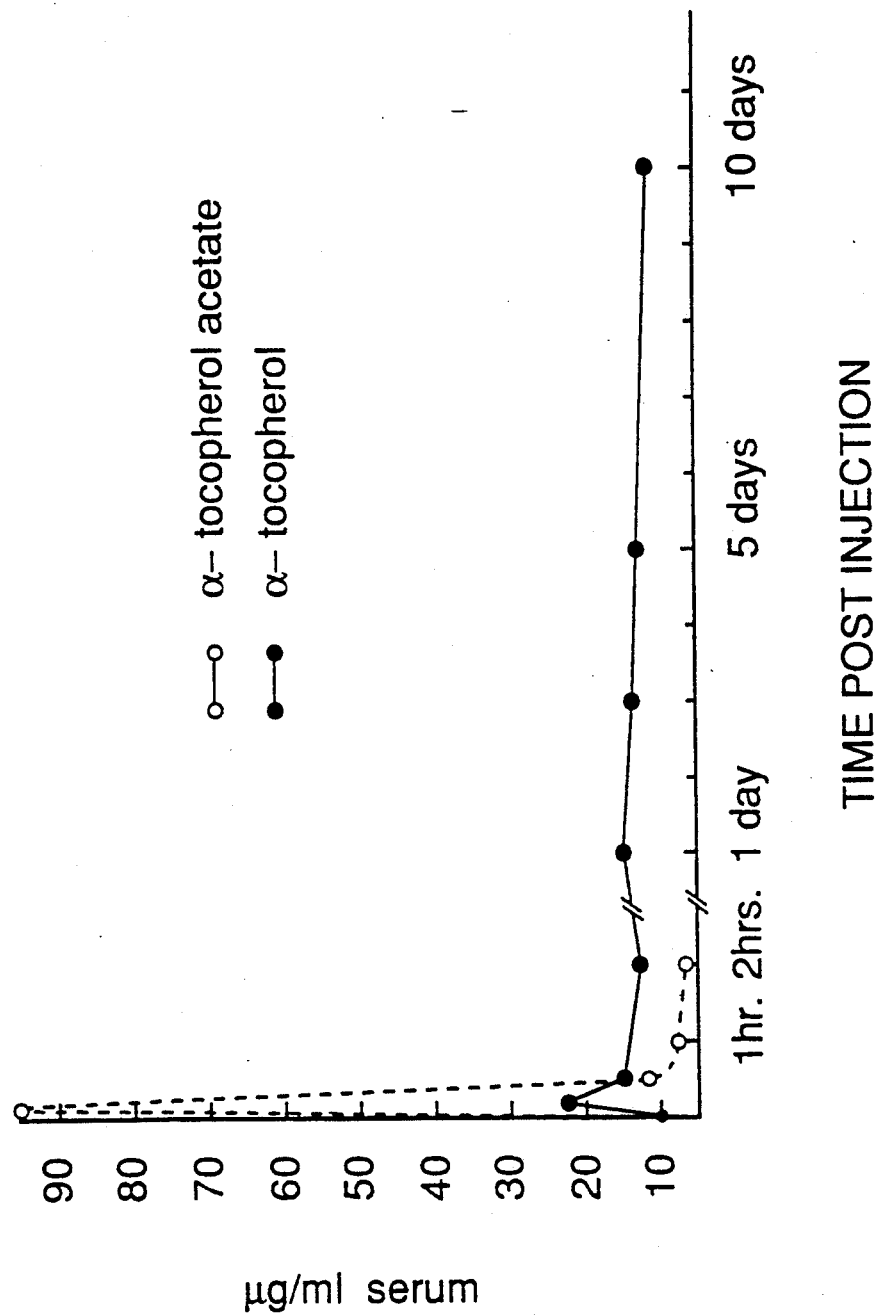
FIG. 2 shows the serum levels of tocopherol and tocopherol acetate administered in a microemulsion injected intravenously into rats.

FIG. 2 shows that serum levels of tocopherol acetate rose abruptly but declined almost immediately to normal. The α-tocopherol levels in serum rose to a lesser extent and then remained slightly above the control level over a period of about ten days.

Figure 3:
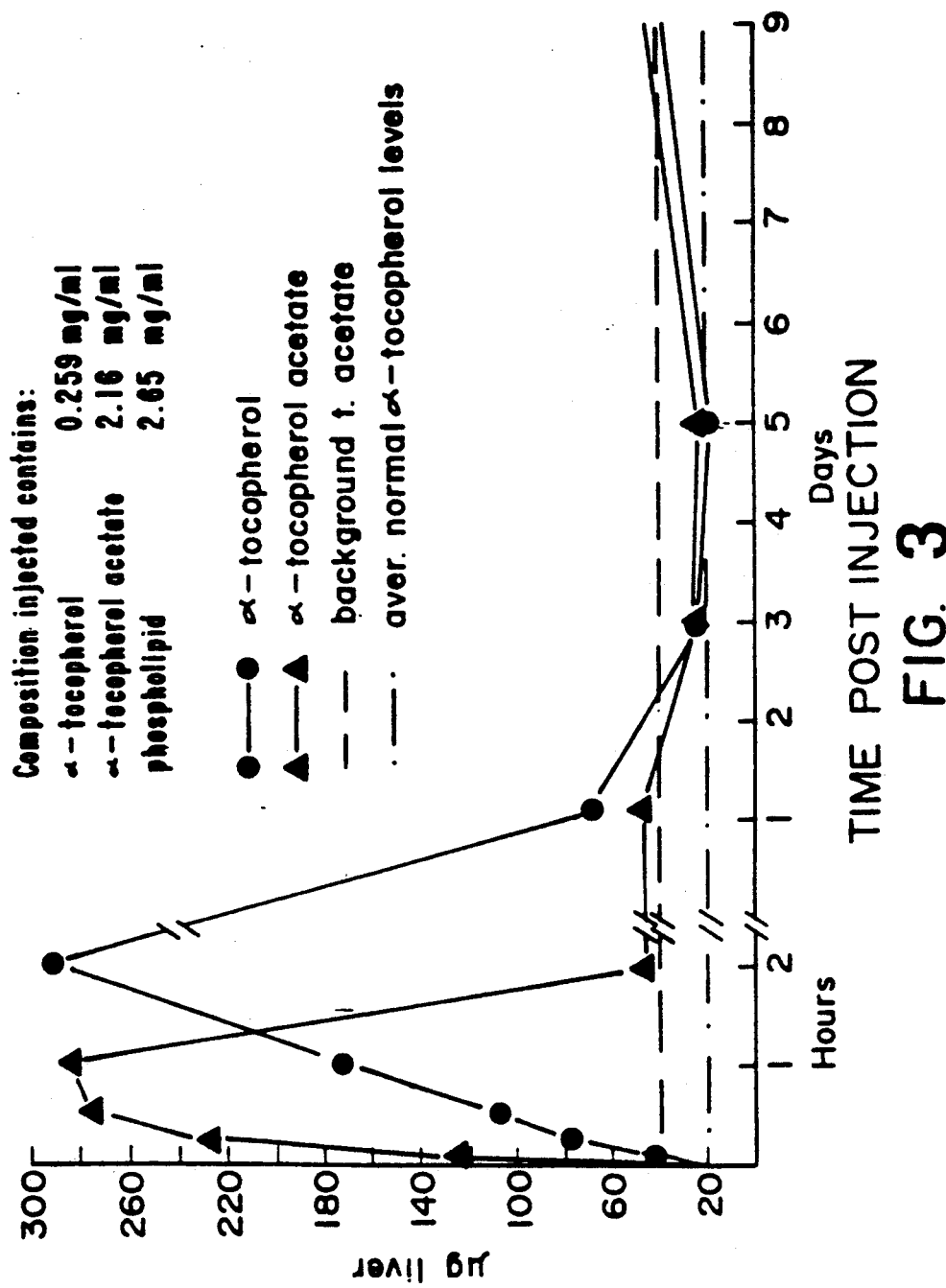
FIG. 3 shows the corresponding levels of tocopherol and tocopherol acetate in liver extracts of the same rats for which results are shown in FIG. 2.

FIG. 3 shows the levels of tocopherol and tocopherol acetate in liver extracts. The concentration of tocopherol acetate in liver rose dramatically but declined almost to normal levels before the end of a two hour period. Lagging, and corresponding to this decrease, was a peak in the tocopherol level in the liver indicating that the tocopherol acetate was completely hydrolyzed after approximately two hours. The tocopherol then disappeared from the liver after about one day, presumably causing the rise in the plasma levels shown in FIG. 2 at that time.

These results show that tocopherol acetate can be used as a source of tocopherol in vivo. Hydrolysis is apparently carried out efficiently by the liver. Therefore microemulsions using tocopherol acetate as active ingredient can be used as a source of vitamin E. The dosage level can thus be elevated by a factor of approximately 10 over that which would have been possible had it been necessary to use tocopherol per se.

EXAMPLE 13

Stability

The microemulsions were assessed for particle size and density as well as composition over a 3 month period. No changes in these parameters were noted.

We claim:

1. An aqueous suspension for the intravenous administration of fat-soluble active ingredient which is a microemulsion of pseudomicelles containing said active ingredient, said pseudomicelles having diameters in the range of 300-1000 and which pseudomicelles are approximately spherical in shape and are comprised of 30-60% of a naturally occurring amphipatic substance as an outer layer surrounding 40-70% of a hydrophobic lipid as a hydrophobic core.

2. The composition of claim 1 wherein the amphipatic substance comprises a phospholipid.

3. The composition of claim 2 wherein the amphipatic substance is lecithin.

4. The composition of claim 3 wherein the lecithin is phosphatidylcholine.

5. The composition of claim 1 wherein the hydrophobic lipid is selected from tocopherol acetate, vitamin A acetate, and triglycerides.

6. The composition of claim 1 wherein the active ingredient is selected from tocopherol, tocopherol acetate, vitamin A, vitamin A acetate, vitamin D, and vitamin K.

7. The composition of claim 6 wherein the active ingredient is selected from tocopherol and tocopherol acetate.

8. The composition of claim 1 which is prepared from a mixture containing 5% tocopherol; 40%-55% hydrophobic lipid; and 45%-55% lecithin.

9. The composition of claim 1 wherein the amphipatic substance is selected from the group consisting of lecithin, cephalin, and sphingomyelin.

10. A method of administering fat-soluble pharmaceuticals which comprises injecting into the venous system of a subject in need of such treatment with an effective amount of the composition of claim 1.

11. A method to prepare the composition of claim 1 which comprises sonicating an aqueous suspension containing a mixture of 40-70% hydrophobic lipid and 30-60% of a naturally occurring amphipatic substance to obtain pseudomicelles, and partitioning the sonicate according to density, and
   selecting the fraction containing pseudomicelles having diameters in the range of 300-1000 Å.

* * * * *